United States Patent [19]
McCulloch et al.

[11] Patent Number: 5,928,515
[45] Date of Patent: Jul. 27, 1999

[54] ADSORPTIVE SEPARATION OF 3-HYDROXYTETRAHYDROFURAN ENANTIOMERS

[75] Inventors: Beth McCulloch, Clarendon Hills; Peter K. Nickl, Des Plaines, both of Ill.

[73] Assignee: UOP LLC, Des Plaines, Ill.

[21] Appl. No.: 08/990,166

[22] Filed: Dec. 12, 1997

[51] Int. Cl.[6] .................................................... B01D 15/08
[52] U.S. Cl. .......................... 210/635; 210/656; 210/659; 210/198.2; 549/475
[58] Field of Search ..................................... 210/635, 656, 210/659, 198.2, 662; 549/475

[56] References Cited

U.S. PATENT DOCUMENTS

| | | | |
|---|---|---|---|
| 3,706,812 | 12/1972 | DeRosset et al. | 260/674 SA |
| 4,129,579 | 12/1978 | Kang | 549/475 |
| 4,533,742 | 8/1985 | Lin | 549/475 |
| 4,539,415 | 9/1985 | Mueller | 549/475 |
| 4,861,872 | 8/1989 | Okamoto | 536/18.7 |
| 4,912,205 | 3/1990 | Okamoto | 536/20 |
| 5,126,055 | 6/1992 | Yamashita et al. | 210/659 |
| 5,354,852 | 10/1994 | Ikeda | 536/17.9 |
| 5,543,506 | 8/1996 | Okamoto | 536/18.7 |
| 5,565,104 | 10/1996 | Priegnitz | 210/659 |
| 5,635,072 | 6/1997 | Moran | 210/659 |
| 5,770,088 | 6/1998 | Ikeda | 210/659 |

OTHER PUBLICATIONS

*A Practical Approach to Chiral Separations by Liquid Chromatography*, edited by G. Subramanian, VCH Publishers, New York, NY, 1994, pp. 124–127 and 8–17.

Optical resolution by simulated moving–bed adsorption technology, authored by Masakazu Negawa and Fumihiko Shoji, *Journal of Chromatography*, 590 (1992) pp. 113–117.

*Primary Examiner*—Ernest G. Therkorn
*Attorney, Agent, or Firm*—Thomas K. McBride; John F. Spears, Jr.

[57] ABSTRACT

The chiral isomers of 3-hydroxytetrahyrofuran are separated by means of liquid chromatography using a stationary phase comprising a substituted polysaccharide carbamate. The separation may be performed using a simulated moving bed adsorbent system. Suitable mobile phase materials comprise a mixture of a light paraffin and a low molecular weight aliphatic alcohol such as a mixture of n-hexane and ethanol. Amylose is the preferred polysaccharide.

11 Claims, No Drawings

ADSORPTIVE SEPARATION OF 3-HYDROXYTETRAHYDROFURAN ENANTIOMERS

FIELD OF THE INVENTION

The subject invention relates to a process for the adsorptive separation of chiral isomers of cyclic hydrocarbons. More specifically, the invention relates to a simulated moving bed process for the separation of isomers of hydroxytetrahydrofuran.

BACKGROUND OF THE INVENTION

Adsorptive separations are employed when it is impractical or impossible to perform a separation using simpler means such as fractional distillation. These separations can be performed using one of more beds of adsorbent operated on a cyclic or swing bed system. However the several benefits provided by continuous operations which provide a uniform product have prompted the development of a process which simulates the continuous countercurrent movement of the adsorbent and process streams. This process technology, known as simulated moving bed (SMB) adsorptive separation, was originally developed as a petroleum refining process to facilitate the removal of straight chain low octane number paraffins from gasoline blending stocks. It, however, found its first large scale commercial application in the separation of longer chain paraffins from kerosene boiling fractions for use in the production of detergent alkylates and in the separation of xylene fractions. Numerous processes are described in the patent literature in which zeolitic adsorbents are used to separate close boiling chemical compounds such as the isomers of dialkyl substituted monocyclic aromatics. For instance the separation of para-xylene from other xylene isomers using simulated moving bed technology is widely described and is now widely practiced commercially in the petrochemicals industry. It is used in the recovery of a large percentage of the para-xylene which is eventually converted into polyester fiber.

More recently it has been discovered that the pharmaceutical effects of various common drugs differs greatly between the different chiral enantiomers of the drug. It has also been found that specific chiral structures are necessary in some drugs now under development for the treatment of a large number of diseases. The separation of enantiomers has therefore become very important in the pharmaceutical industry, and the methods used in other industries to separate compounds having similar physical characteristics are being refined to perform the separation of chiral compounds. Small scale SMB units adapted to the particular needs of the pharmaceutical industry are therefore being developed. There still remains the continuing need to develop the specific stationary phase/mobile phase pairs needed to effect the various desirable separations by adsorption.

RELATED ART

U.S. Pat. No. 3,706,812 issued to A. J. de Rosset et al describes a small scale SMB adsorptive separation apparatus which is described as being suitable for use in small scale separations such as performed in the pharmaceutical industry.

U.S. Pat. No. 5,126,055 issued to A. Yamashita et al describes the separation of chiral compounds using a simulated moving bed adsorptive separation method. This technology was first described in a presentation at PREP '91 held in Arlington, Va., USA in May 1991 and printed at the Journal of Chromatography, 590 (1992) pages 113–117.

Several other different designs for small scale SMB units have been developed. For instance, U.S. Pat. No. 5,565,104 issued to J. W. Priegnitz describes a small scale SMB unit design employing five rotary valves to interconnect the chambers containing the adsorbent used in the process. U.S. Pat. No. 5,635,072 issued to M. G. Moran illustrates another mechanical arrangement which can be employed to perform an SMB process. This arrangement uses a large number of multiport valves to direct fluid flow to and from header lines and thus does not require rotary valves having a large number of ports. This patent also describes a unique pressure pairing arrangement at the valve ports to decrease products contamination.

A large number of chiral stationary phases have been developed and many of them are available commercially. A detailed description of one representative substituted cellulose carbamate is provided by U.S. Pat. No. 5,543,506 issued to Y. Okamoto. A description of several different stationary phases of this type is provided at pages 124–127 of *A Practical Approach to Chiral Separations by Liquid Chromatography* edited by G. Subramanian, VCH Publishers, New York, N.Y., 1994.

A method of classifying the various types of chiral stationary phases is presented at pages 8–17 of this same text. This method is used in the following description of the invention.

SUMMARY OF THE INVENTION

The invention is the discovery that it is possible to separate hydroxytetrahydrofuran enantiomers by adsorptive separation despite the lack of significant functionality such as acid or base groups in this compound's structure. More specifically the invention is a simulated moving bed process for the adsorptive separation of 3-hydroxytetrahydrofurans. One broad embodiment of the invention may be characterized as a process for the adsorptive separation of a desired hydroxytetrahydrofuran isomer from a feed mixture comprising at least a first and a second hydroxytetrahydrofuran isomer which process comprises contacting said feed mixture with an adsorbent comprising an inorganic oxide supported substituted carbamate at adsorption conditions and effecting the adsorption of the first hydroxytetrahydrofuran isomer by said adsorbent and the production of a raffinate stream comprising the second hydroxytetrahydrofuran isomer; and subsequently contacting said adsorbent with a desorbent comprising a low molecular weight alcohol at desorption conditions including a substantially constant temperature to effect the removal of the desired isomer from said adsorbent as an extract stream, and recovering the first isomer.

DETAILED DESCRIPTION AND PREFERRED EMBODIMENTS

Hydroxytetrahydrofuran (HTHF) is a cyclic compound having the structure shown below.

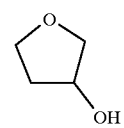

It has utility as a chemical intermediate useful in the preparation of many desired compounds. For instance, the isomers of hydroxytetrahydrofuran are being used in and researched for the production of reverse transcriptase inhibitors and protease inhibitors useful in therapeutic drugs for the treatment AIDS related illnesses. It is therefore desired to produce pure HTHF enantiomers. It is also desirable to reduce the cost of performing the various separation steps inherent in the production of these compounds.

While the asymmetrical synthesis of optically pure hydroxytetrahydrofurans is very difficult, the production of racemic mixtures (mixtures having equal concentration of the isomers) is quite easy. Unfortunately it is difficult to resolve the HTHF isomers of this racemic mixture by conventional means such as crystallization in optically active solvents or by crystallization of diastereomeric salts.

It is therefore an objective of the subject invention to provide a process for the separation of HTHF isomers. It is a specific objective of the subject invention to provide a process for the adsorptive separation of 3-hydroxytetrahydrofuran isomers.

It was believed that since the HTHF molecule does not have acid or base groups and has very little functionality it would be very difficult to separate the enantiomers by adsorptive separation. However, it has surprisingly been discovered that HTHF isomers can be effectively separated from a racemic mixture by the use of a specific stationary/mobile phase system countercurrent, preferably using simulated moving bed adsorptive separation technology.

While the bulk of the discussion herein is directed to the separation of the enantiomers of 3-hydroxytetrahydrofuran, the feed to the process can comprise other related compounds including alkyl substituted hydroxytetrahydrofurans such as mono and di methyl hydroxytetrahydrofurans, dihydroxytetrahydrofurans and similar related compounds having the furan cyclic structure. The preferred isomer for recovery is the S enantiomer of HTHF.

The subject invention can be practiced in a fixed or a moving adsorbent bed system. For instance the process can be performed using a single bed of adsorbent. Alternatively flows could be switched between two or more beds of adsorbent in separate chambers in a cyclic pattern. The preferred system for practicing this process is a countercurrent simulated moving bed system, such as described in U.S. Pat. No. 2,985,589, incorporated herein by reference for its teaching in the practice of simulated moving bed adsorptive separation processes. SMB systems have numerous advantages over batch-type processes. An SMB process produces a constant uniform composition product. It is flexible and the recovery and purity of the product can normally be adjusted.

An SMB process apparatus comprises many serially-connected adsorbent beds with intermediate points for the appropriate addition or removal of feed, extract, desorbent and raffinate streams. Cyclic advancement of the input and output streams through the apparatus can be accomplished by a multiple valve manifold system or by rotary disc valves as shown in U.S. Pat. Nos. 3,040,777 and 3,422,848. In these simulated moving bed systems the adsorbent is divided between eight or more subbeds. Equipment utilizing these SMB principles can vary in size from the pilot plant scale shown in previously cited U.S. Pat. No. 3,706,812 to very large scale petrochemical units. Feed stream flow rates can therefore range from a few cc per hour to many thousands of gallons per hour. The invention may also be practiced in a cocurrent, pulsed batch process, like that described in U.S. Pat. No. 4,159,284 or in a cocurrent, continuous process, like that disclosed in U.S. Pat. Nos. 4,402,832 and 4,478,721.

The functions and properties of adsorbents and desorbents in the chromatographic separation of liquid components are well-known, and reference may be made to U.S. Pat. No. 4,642,397, which is incorporated herein, for additional description of these adsorption fundamentals. The SMB technology originated in the petrochemical industry and has slightly different nomenclature than used in classical chromatography. For instance, the mobile phase of chromatography is referred to as the desorbent of an SMB system. Likewise the stationary phase of chromatographer's lexicon is the adsorbent of an SMB system. These terms are used interchangeably herein. The interchangeability of the nomenclature is in part a recognition that the separation of chiral isomers through use of SMB technology is fundamentally no different in principle from the separation of any other type of isomer. The most difficult part is finding an effective adsorbent/desorbent system and suitable conditions.

During the adsorption step of the SMB separation process, a feed mixture containing a mixture of the isomers to be separated is contacted with an adsorbent at adsorption conditions. The desired isomer is selectively adsorbed and retained by the adsorbent while the other components of the feed mixture such as other isomers are less highly unabsorbed. The adsorbent containing the more selectively adsorbed isomer is referred to as a "rich" adsorbent; that is, containing a near equilibrium loading of the more selectively adsorbed isomer. The unabsorbed (raffinate) components of the feed mixture are then removed from the interstitial void spaces between the particles of adsorbent and from the surface of the adsorbent by a flushing action. The adsorbed isomer is then recovered from the rich adsorbent by contacting the rich adsorbent with a single stream comprising a desorbent material at desorption conditions. The desorbent displaces the desired isomer which enters the flowing liquid to form an extract stream. The extract stream is transferred to a product recovery zone for recovery of the desired isomer. In the subject process only the desired isomer is retained on the adsorbent and only a single extract stream is produced.

The key to any successful adsorptive separation is the use of an effective adsorbent/desorbent system. Adsorbents to be used in the process of this invention include certain of the polysaccharide-based materials as described on pages 377 and 378 of the previously-cited text by Subramanian. In these adsorbents, the material active for the separation is actually a thin layer supported on very small particles of microporous inorganic oxide, preferably silica. The active layer comprises a polymer coating formed from either cellulose or amylose. This polymer is then converted to an ester, carbamate or ether derivative. The most effective adsorbent located and therefore the preferred adsorbent is amylose tris (3,5-dimethyl phenyl carbamate). An adsorbent of this nature is marketed by Daicel Chemical Industries under the trademark Chiralpak AD.

The stationary phase of a HPLC column is normally in the form of very small particles tightly packed within a single metal column. In larger scale units SMB units, larger less densely-packed particles are placed in a number of different adsorbent chambers or in a number of separate beds within a larger chamber. The adsorbent particles used in some separations will contain the actual adsorbent dispersed in an amorphous inorganic matrix or binder having channels and cavities therein which enable liquid access to the crystalline material. Chiral stationary phase (CSPs) are not normally of this nature. Most CSPs contain an organic moiety coated or bonded onto a support. Preferably the CSP support is small diameter silica spheres. Methods for forming traditional non-CSP adsorbent material into particles can be used to form a CSP support if desired. These methods include forming a wet mixture with an inorganic binder, generally a clay comprising a silicon dioxide and aluminum oxide. The binder aids in forming or agglomerating smaller particles which otherwise would comprise a fine powder. The blended mixture is extruded into cylindrical pellets or formed into beads which are subsequently calcined in order to convert the binder into an amorphous material of considerable mechanical strength. The adsorbent particles may thus be in the form of extrudates, tablets, macrospheres or granules having a desired particle range, preferably from about 16 to about 60 mesh (Standard U.S. Mesh) (1.9 mm to 250 microns). Clays of the kaolin type, water permeable organic polymers or silica are generally used as binders. It is also possible to use other suitable forms of adsorbent. The preferred adsorbents are not bound in this nature but are built upon a homogeneous solid support, preferably an inorganic oxide such as silica or alumina.

If the particles contain a binder, the active chiral stationary phase material will ordinarily be present in the formed adsorbent particles in amounts ranging from about 75 to about 98 wt. % of the particle based on volatile-free composition. Volatile-free compositions are generally determined after the adsorbent has been calcined at 900° C. in order to drive off all volatile matter. It is recognized most CSPs are very temperature sensitive and would be destroyed at this temperature as the organic moiety which provides chiral recognition would decompose. However, a volatile-free state provides a frame of reference for measurement of the support composition. The remainder of the adsorbent particle will generally be an inorganic matrix present in intimate mixture with the small particles of the stationary phase material.

In the subject invention the separation of a desired isomer is effected by passing a feed mixture comprising two or more isomers over a bed of an adsorbent which selectively retains the desired isomer while permitting other components of the feed stream to pass through the adsorption zone more quickly in an unchanged condition. The flow of the feed mixture is stopped and the adsorption zone is then flushed to remove nonadsorbed materials surrounding the adsorbent. Thereafter the desired isomer is desorbed from the adsorbent by passing a desorbent (mobile phase) stream through the adsorbent bed, with the desorbent material comprising an aromatic hydrocarbon described herein. The desorbent material is commonly also used to flush nonadsorbed materials from the void spaces around and within the adsorbent Although a multicomponent desorbent is used in the subject process, preferably only a single desorbent stream is employed. The composition, temperature and strength of the desorbent stream preferably remain constant during the desorption step, but can vary slightly due to the cyclic nature of the composition of raffinate and extract streams.

For purposes of this invention, various terms used herein are defined as follows. A "feed mixture" is a mixture containing one or more extract components and one or more raffinate components to be separated by the process. The term "feed stream" indicates a stream of a feed mixture which passes into the adsorbent used in the process.

An "extract component" is a compound or class of compounds that is more selectively adsorbed by the adsorbent while a "raffinate component" is a compound or type of compound that is less selectively adsorbed. The term "desorbent material" shall mean generally a material capable of desorbing an extract component from the adsorbent. The term "raffinate stream" or "raffinate output stream" means a stream in which a raffinate component is removed from the apparatus. The composition of the raffinate stream can vary from essentially 100% desorbent material to essentially 100% raffinate components. The term "extract stream" or "extract output stream" shall mean a stream in which an extract material which has been desorbed by a desorbent material is removed from the apparatus. Due to the cyclic steps of the process, the composition of the extract stream can vary as it is withdrawn from essentially 100% desorbent material to essentially 100% extract components. Typically at least a portion of the extract stream and the raffinate stream are passed to separation means, normally evaporators or crystallizers but possibly a fractional distillation column, wherein at least a portion of desorbent material is recovered. This will also produce an extract product and possibly a raffinate product. The terms "extract product" and "raffinate product" mean products produced by the process and containing, respectively, an extract component and a raffinate component in higher concentrations than those found in the extract stream and the raffinate stream. The solubility of many enantiomers is limited in such mobile phases as a hexanelalcohol mixture. The term "rich" is therefore intended to indicate a relatively low concentration of the indicated compound or class of compounds which is measured relative to other internal process streams. A concentration greater than twice that of a precursor stream is considered as being rich as that term is used herein. A concentration greater than 5 mole percent may be "rich" on this basis.

Selectivity for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. This can be expressed in terms of time or volume of the process stream between these points. Selectivity is traditionally given as $\beta$ in SMB literature and as alpha in chromatography literature. Where selectivity of two components approaches there is no preferential adsorption of one component by the adsorbent with respect to the other; they are both adsorbed to about the same degree with respect to each other. While separation of an extract component from a raffinate component is theoretically possible when the selectivity of the adsorbent for the extract component with respect to the raffinate component is not much greater than 1, it is preferred that such selectivity approach a value of 2. Analogous to relative volatility in fractional distillation, the higher the selectivity, the easier the adsorptive separation is to perform. Higher selectivities permit a smaller amount of adsorbent to be used.

The rate of exchange of an extract component with the desorbent can generally be characterized by the width of the peak envelopes at half intensity obtained from plotting the composition of various species in the adsorption zone effluent during a pulse test versus time. The narrower the peak width, the faster the desorption rate. The rate of exchange of various components can be expressed as "stage time" which is calculated from the net retention volume and the half width peaks of the components according to the formula in *Principles of Adsorption and Adsorption Processes* by Douglas M. Ruthven, published by John Wiley & Sons, 1984. The desorption rate can also be characterized by the distance between the center of a tracer peak envelope and the disappearance of an extract component which has just been desorbed. This distance is the volume of desorbent pumped during this time interval.

The relative performance of adsorbent/desorbent pairs is measured in terms of speed and selectivity. The "speed" of the adsorption steps at various conditions or for different adsorbent/desorbent combinations can be measured and compared as stage times. Stage times are normally inversely correlated with temperature. That is, as the temperature goes up, the stage times normally go down. A higher temperature is therefore normally desired since low stage times mean a smaller, less expensive plant is required to separate a given quantity of feed material. On the other hand selectivity is normally negatively impacted by higher temperatures. That is, selectivity normally decreases as the temperature goes up. In designing a commercial scale separation unit of this type, it is therefore necessary to choose operating conditions based upon a balance or trade-off of stage times versus selectivity.

An important characteristic of an adsorbent/desorbent pair is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process. Ideally, desorbent materials should have a selectivity equal to about 1 or slightly less than 1 with respect to all extract components so that all of the extract components can be desorbed as a class with reasonable flow rates of desorbent material, and so that extract components can displace desorbent material in a subsequent adsorption step.

In simulated moving bed adsorptive separation processes, which are generally operated continuously at substantially constant pressures and temperatures which insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. Finally, desorbent materials should be readily available and reasonable in cost.

The desorbent material of the mobile phase will have to be selected in each instance based upon the above criteria and its performance with the stationary phase. The preferred desorbent material of the subject invention is a light or low molecular weight alcohol, which terms are used herein to refer to alcohols having less that nine carbon atoms per molecule. Light aliphatic alcohols are preferred with suitable examples including methanol, ethanol, propanol, isopropanol, 1-butanol, sec butanol, tertiary butanol and pentanol. The alcohols are normally rather strong in their activity as desorbents and it is customary to dilute the alcohol with a compatible light paraffin which is inert in the system. Hexane is a customary diluent. Other light paraffins such as pentane or heptane could also be used if desired. The alcohol concentration in the mobile phase will normally be on the order of 5–60 vol. percent with a concentration of 10–30 percent being preferred.

It is expected that the feed mixtures charged to the process will be obtained from an upstream synthesis step with one or more separation steps having been performed on the effluent of the synthesis procedure. Feed mixtures which can be utilized in the process of this invention comprise at least a first 3-hydroxytetrahyrofuran isomer and one other 3-hydroxytetrahyrofuran isomer. The feed stream may also contain one or more other compounds which are unseparated impurities, by-products of prior production steps, or solvents. Some of these compounds can be relatively innocuous. Other compounds could be highly undesirable. Thus, the feed mixture charged to the process of this invention can contain a sizable number of different compounds. It is preferable to maintain these other compounds at a minimum concentration in order to prevent contamination of the product of this process by compounds which are not selectively adsorbed. The feed concentration of HTHF is limited by its solubility in the mobile phase. The maximum solubility in a 90/10% hexane/ethanol mixture is about 9.3 wt. % at typical conditions. It is expected that the hydroxytetrahydrofuran isomers will be present in the feed stream in a concentration on the order of only about 2.0 to 8.0 wt. percent. HTHF solubility increases with higher alcohol contents and higher HTHF concentrations are possible.

Those skilled in the art will appreciate that the performance of an adsorbent may be greatly influenced by a number of factors not related to its composition such as operating conditions, feed stream composition, water content and desorbent composition. Adsorption conditions used in the subject process include a broad temperature range of from about 20 to about 250° C. A temperature of about 25 to about 100° C. is preferred. The process is operated at a pressure sufficient to maintain liquid phase conditions, which may be from about atmospheric to 1500 psig. Desorption conditions include this same range of temperature and pressure as used for adsorption conditions. Specifically the adsorption and desorption steps are preferably performed at substantially the same temperature. Further the temperature is preferably not varied between or within beds of adsorbent. The temperature is therefore uniform and constant throughout the adsorbent chamber(s) during the process. The adsorbent chambers may be maintained at a different temperature from storage tanks or reaction zones used in the process. The pressure in an SMB process may vary greatly between different points in an SMB apparatus due to the pressure drop across the beds of densely packed small diameter adsorbent normally used in the process. References to pressure therefore refer to the inlet pressure of the feed stream.

It is also possible to test the performance of a mobile/stationary phase system in a conventional high performance liquid chromatography (HPLC) apparatus However, a dynamic testing apparatus is preferably employed to test the ability of a particular stationary/mobile phase combination to effectively separate a particular feed mixture. One such test apparatus is that used to perform a pulse test. This "pulse test" apparatus consists of a helical adsorbent chamber of approximately 70 cc volume having inlet and outlet portions at opposite ends of the chamber. The tubular chamber is contained within a temperature control means and, in addition, pressure control equipment is used to operate the chamber at a constant predetermined pressure. Quantitative and qualitative analytical equipment, such as refractometers, polarimeters, chromatographs, etc., can be attached to the outlet line of the chamber and used to analyze the effluent stream leaving the adsorbent chamber.

During a pulse test the following general procedure is used to obtain data; e.g., selectivities, for various adsorbent/desorbent systems. The adsorbent is filled to equilibrium with a particular desorbent by passing the desorbent material through the adsorbent chamber. At a convenient time, a pulse of feed containing known concentrations of a tracer and of a particular extract component or a raffinate component, or both, diluted in desorbent material is injected for a duration of several minutes. Desorbent flow is resumed, and the tracer and the extract and raffinate components are eluted as in a liquid-solid chromatographic operation. The effluent can be analyzed by on-stream chromatographic equipment and traces of the envelopes of corresponding component peaks developed. Alternatively, effluent samples can be collected periodically and later analyzed separately as by gas chromatography.

From information derived from the test, adsorbent/desorbent system performance can be rated in terms of void volume, retention volume for an extract or a raffinate component, and the rate of desorption of an extract component from the adsorbent and selectivity. Void volume is the non-selective volume of the adsorbent, which is expressed by the amount of desorbent pumped during the interval from initial flow to the center of the peak envelope of the tracer. The net retention volume of an extract or a raffinate component may be characterized by the distance between the center of the peak envelope (gross retention volume) of the extract or raffinate component and the center of the peak envelope (void volume) of the tracer component or some other known reference point. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent material pumped during this time interval. Selectivity can be determined by the ratio of the net retention volumes of the more strongly adsorbed component to each of the other components.

EXAMPLES

The experiments reported below summarize a number of pulse tests performed using preloaded HPLC columns. The tests were intended to evaluate the ability of different adsorbent/desorbent combinations to separate the HTHF enantiomers. The test results are provided to illustrate the process and are not intended to restrict the scope of the claims.

For each test the column was maintained at a constant temperature of 25° C. and at a pressure of approximately 100 psig to maintain liquid-phase operations. The composition of the effluent stream was monitored by refractive index as the lack of a chromophore in HTHF made it impossible to use UV analytical equipment. The feed mixture employed for each test was a mixture containing 0.3 wt. % 3-hydroxytetrahydrofuran dissolved in the mobile phase. Such small feed quantities are customary with HPLC columns used for analytical work. A small quantity of the feed is desired because the columns contain only a very small amount of the stationary phase and the stationary phase has a very small capacity for the feed compound. Different feed solutions were made for each mobile phase tested. The flow rate through the HPLC column was 1 ml/min and the injection volume was 10 microliters. Tri-tertbutylbenzene was used as a tracer in some of the runs. The compositions of the mobile phase and stationary phase for each test is given in Table 1.

The first eight runs were performed with type II chiral stationary phases supplied by Daicel Chemical Company. The CSP of run 9 was a type I chiral phase in which the chiral moiety is bonded via a non-chiral spacer to a silica support. This CSP is sold under the trademark Whelk-O 1 by Regis Technologies Inc. of Morton Grove, Ill. It is described as a Pirkle-concept stationary phase having both π-acceptor and π-donor characteristics and derived from 4-(3,5-dinitrobenzamido)-tetrahydrophenathrene covalently bound to 5 µm silica particles. The CSP of run 10 was a type III beta-cyclodextrin material sold as Cyclobond I 2000 by ASTEC. The distinguishing feature of this class of phases is that the mechanism of chiral discrimination involves inclusion of the solute within a chiral cavity. Cyclobond I 2000 CSP has an S-naphthylethyl carbamate group attached to a betacyclodextrin containing seven glucose residues and forming a hydrophobic cavity.

The operations performed during a test were as follows: The mobile phase was run continuously through the test apparatus at the set flow rate. At some convenient time, the mobile phase flow was stopped and the feed mixture was injected into the column. The flow of the desorbent stream was then resumed and continued through the adsorbent column until all of the feed compounds had been eluted from the column as determined by automated analysis of the effluent material leaving the adsorption column. This typically occurred within less than 15 minutes.

Table 1 gives the results of the tests. The identity of the stationary phase is given below the table. The entries under the Mobile Phase heading give the relative volumetric proportions of the two components in the Mobile Phase. The nomenclature $C_6$ indicates hexane; EtOH refers to ethanol; IPA refers to isopropanol and EtOAc refers to ethyl acetate. $RT_1$ is the retention time of the first enantiomer to elute. $RT_2$ is the retention time of the second enantiomer to elute. $k_1$ is a "capacity factor" for the first enantiomer to elute. $k_2$ is a capacity factor for the second enantiomer to elute. Alpha is a measure of performance of the system defined as $k_2'/k_1'$ and is a measure of the separation provided by the system. These are calculated in accordance with *Modern Practice of Liquid Chromatography*, ed. J. J. Kirland, Wiley, New York (1971). The tracer used in the tests was "TTBB" a standard test material more formally described as tri-tert-butylbenzene.

The test results indicate the CSP/mobile phase systems used in the first six reported runs gave a separation of the 3-HTHF isomers which could be used to perform a successful separation as by SMB technology. The other CSP/mobile phase systems did not provide a useful separation, with runs 8–10 showing essentially no separation of the isomers.

| Run No. | Stationary Phase | Mobile Phase | $RT_1$ | $RT_2$ | $k_i$ | $k_2$ | Alpha |
|---|---|---|---|---|---|---|---|
| 1 | 1 | 90/10 $C_6$/IPA | 7.51 | 8.85 | 1.38 | 1.80 | 1.31 |
| 2 | 1 | 95/5 $C_6$/IPA | 12.86 | 16.26 | 3.07 | 4.15 | 1.35 |
| 3 | 1 | 90/10 $C_6$/EtOH | 9.46 | 12.13 | 1.99 | 2.84 | 1.42 |
| 4 | 1 | 95/5 $C_6$/EtOH | 16.25 | 21.93 | 4.14 | 5.94 | 1.43 |
| 5 | 1 | EtOH | 3.68 | 3.83 | 0.16 | 0.21 | 1.31 |
| 6 | 1 | 85/15 EtOH/EtOAc | 3.60 | 3.76 | 0.14 | 0.19 | 1.38 |
| 7 | 2 | 90/10 $C_6$/IPA | 6.81 | 7.09 | 1.23 | 1.32 | 1.08 |
| 8 | 3 | 90/10 $C_6$/IPA | 6.40 | 6.41 | 1.07 | 1.08 | 1.00 |
| 9 | 4 | 90/10 $C_6$/IPA | 19.37 | 19.56 | 5.09 | 5.15 | 1.01 |
| 10 | 5 | 90/10 $C_6$/IPA | 10.40 | 1.43 | 2.49 | 2.50 | 1.00 |

Stationary Phase Key
1 Chiralpak AD
2 Chiralcel OD
3 Chiralcel OJ
4 Whelk-O
5 Cyclobond I 2000

The data in the table indicates acceptable separations were obtained with the Chiralpak AD stationary phase when either isopropanol or ethanol, diluted with hexane, are employed as the mobile phase. While a higher degree of separation would be preferable, as shown by an alpha above about 1.5 the observed separation is sufficient to allow adequate separation in a simulated moving bed system.

What is claimed is:

1. A process for the adsorptive separation of a desired hydroxytetrahydrofuran isomer from a feed mixture comprising at least a first and a second hydroxytetrahydrofuran isomer, which process comprises contacting said feed mixture with an adsorbent comprising a supported substituted polysaccharide carbamate at adsorption conditions and effecting the adsorption of the first hydroxytetrahydrofuran isomer by said adsorbent and the production of a raffinate stream comprising the second hydroxytetrahydrofuran isomer; and subsequently contacting said adsorbent with a desorbent comprising a low molecular weight alcohol at desorption conditions including a substantially constant temperature to effect the removal of the desired isomer from said adsorbent as an extract stream, and recovering the first isomer.

2. The process of claim 1 wherein the adsorption and desorption conditions include a substantially equal temperature.

3. The process of claim 1 wherein the desorbent comprises isopropyl alcohol.

4. The process of claim 1 wherein the desorbent comprises ethyl alcohol.

5. The process of claim 1 wherein the desorbent comprises a $C_5$–$C_7$ paraffin and ethyl alcohol.

6. The process of claim 1 wherein the desorbent comprises less than 25 vol % alcohol.

7. A continuous simulated moving bed process for the adsorptive separation of a first 3-hydroxtetrahydrofuran isomer from a feed mixture comprising the first 3-hydroxytetrahydrofuran isomer and at least one other 3-hydroxytetrahydrofuran isomer, which process comprises contacting said feed mixture with a bed of an adsorbent comprising a substituted amylose carbamate at adsorption conditions and effecting the adsorption of the first 3-hydroxytetrahydrofuran isomer by said adsorbent and the production of a raffinate stream comprising the other isomer; and subsequently contacting said bed of adsorbent with a single desorbent stream comprising about 5 to about 25% aliphatic alcohol at desorption conditions which include a substantially constant temperature equal to the temperature of the adsorption conditions to effect the removal of the first 3-hydroxytetrahydrofuran isomer from said adsorbent as a component of an extract stream, and recovering the first 3-hydroxytetrahydrofuran isomer.

8. The process of claim 7 wherein the desorbent also comprises a $C_5$–$C_7$ paraffin.

9. A continuous simulated moving bed process for the adsorptive separation of a first 3-hydroxytetrahydrofuran isomer from a feed mixture comprising the first 3-hydroxytetrahydrofuran isomer and at least one other 3-hydroxytetrahydrofuran isomer, which process comprises contacting said feed mixture with a bed of an adsorbent comprising a substituted carbamate at adsorption conditions and effecting the adsorption of the first 3-hydroxytetrahydrofuran isomer by said adsorbent and the production of a raffinate stream comprising said other isomer; and subsequently contacting said bed of adsorbent with a single desorbent stream comprising a $C_5$–$C_7$ paraffin and about 5 to about 25% aliphatic alcohol at desorption conditions which include a substantially constant temperature equal to the temperature of the adsorption conditions to effect the removal of the first 3-hydroxytetrahydrofuran isomer from said adsorbent as a component of an extract stream, and recovering the first 3-hydroxytetrahydrofuran isomer.

10. The process of claim 9 wherein the adsorbent comprises an amylose tris (3,5-dimethyl phenyl carbamate).

11. The process of claim 9 where the feed mixture comprises less than 5 wt. % hydroxytetrahydrofuran.

* * * * *